(12) United States Patent
Hanemoto et al.

(10) Patent No.: US 12,718,706 B2
(45) Date of Patent: Aug. 25, 2026

(54) TRAINING DEVICE FOR OPHTHALMIC SURGERY

(71) Applicant: MANI, INC., Utsunomiya (JP)

(72) Inventors: Tsukasa Hanemoto, Mito (JP); Akira Hirata, Fukuoka (JP); Yoshiyuki Tazawa, Utsunomiya (JP); Keisuke Tsunoda, Utsunomiya (JP)

(73) Assignee: MANI, INC., Utsunomiya (JP)

( * ) Notice: Subject to any disclaimer, the term of this patent is extended or adjusted under 35 U.S.C. 154(b) by 588 days.

(21) Appl. No.: 17/099,575

(22) Filed: Nov. 16, 2020

(65) Prior Publication Data

US 2021/0150938 A1 May 20, 2021

(30) Foreign Application Priority Data

Nov. 18, 2019 (JP) ................................ 2019-208052
Oct. 9, 2020 (JP) ................................ 2020-171413

(51) Int. Cl.
*G09B 23/30* (2006.01)
*A61F 9/007* (2006.01)

(52) U.S. Cl.
CPC ............ *G09B 23/306* (2013.01); *A61F 9/007* (2013.01)

(58) Field of Classification Search
CPC .............................. G09B 23/306; A61F 9/007
USPC .......................................................... 434/271
See application file for complete search history.

(56) References Cited

U.S. PATENT DOCUMENTS 6,589,057 B1 * 7/2003 Keenan .................. G09B 23/30 434/271
8,845,334 B1 * 9/2014 Stoll ...................... G09B 23/28 434/270
2013/0030524 A1 * 1/2013 Akura .................... G09B 23/34 264/2.7
2016/0063898 A1 * 3/2016 Bernal ................ G09B 23/306 434/271

(Continued)

FOREIGN PATENT DOCUMENTS

EP 1193664 A2 4/2002
WO 2010084595 A1 7/2010
WO 2015151939 A1 4/2017

OTHER PUBLICATIONS

"A Simulated Eye for Vitreous Surgery Using Japanese Quail Eggs," Hirata et al., Graefes Arch Clin Exp Ophthalmol, vol. 251, pp. 1621-1624, Jan. 5, 2013 (Year: 2013).*

(Continued)

*Primary Examiner* — Peter S Vasat
(74) *Attorney, Agent, or Firm* — CHRISTENSEN O'CONNOR JOHNSON KINDNESS PLLC

(57) ABSTRACT

The purpose of the present invention is to provide a training device for ophthalmic surgery so as to make it possible to readily practice inner limiting membrane peeling by using a simulated eye including a Japanese quail eggshell. This training device 1 for ophthalmic surgery includes a base 10 with a hollow portion 11 and a soft simulated sclera member 20 shaped like a part of sphere, wherein the hollow portion 11 is tapered from an upper side to a lower side and houses, upon use, a simulated eye 50 including an eggshell; the simulated sclera member 20 is provided on an upper side of the base 10; and a surgical instrument can contact, through the simulated sclera member 20, an inner surface of the simulated eye 50.

5 Claims, 8 Drawing Sheets

(56) References Cited

U.S. PATENT DOCUMENTS

2016/0098944 A1* 4/2016 Lin .................... G09B 23/32
434/271

OTHER PUBLICATIONS

Hirata, A., et al., "A simulated eye for vitreous surgery using Japanese quail eggs", Graefe's Archive for Clinical and Experimental Ophthalmology, 2013, 251(6), 1621-1624.
Extended European Search Report mailed Feb. 23, 2021, issued in corresponding Application No. 20208185.7, 7 pages.
Extended European Search Report mailed Jan. 19, 2024, issued in corresponding European Application No. EP23205967, filed Nov. 17, 2020, 8 pages.

* cited by examiner

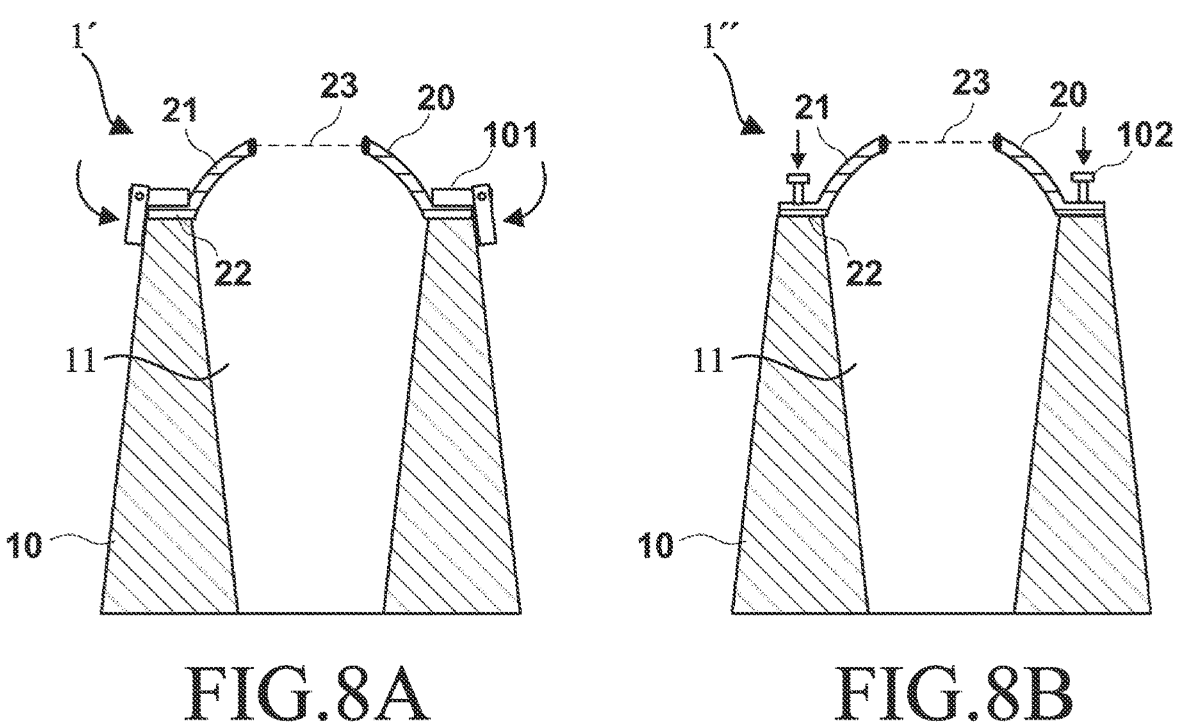
FIG.8A
FIG.8B
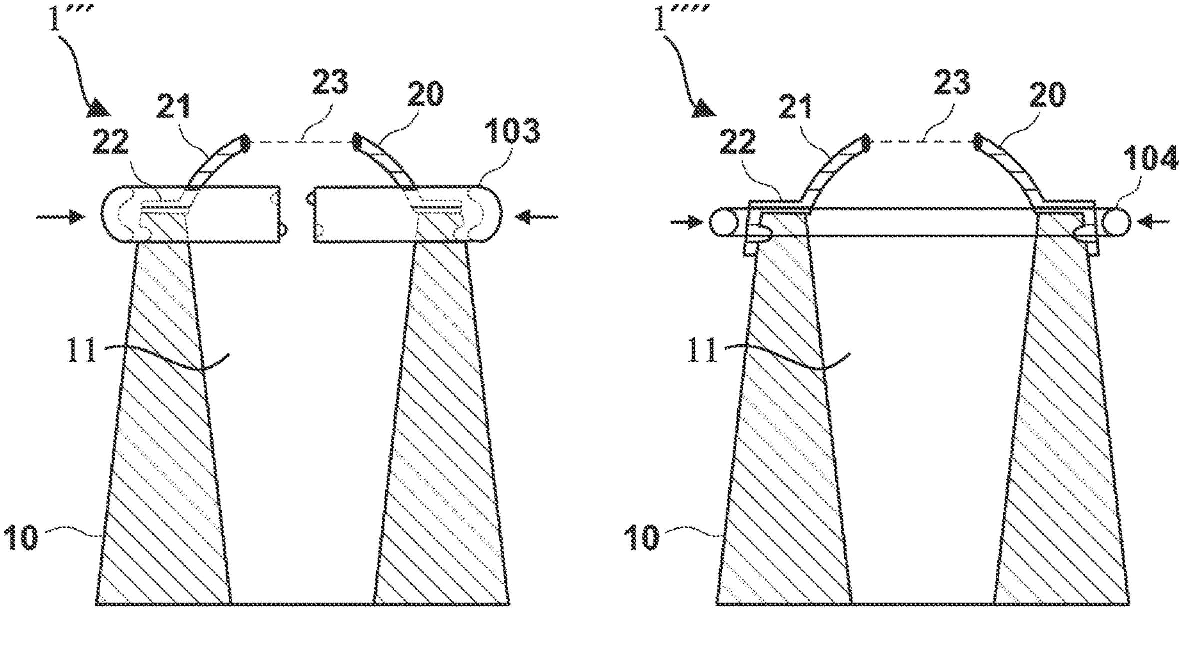
FIG.8C
FIG.8D

TRAINING DEVICE FOR OPHTHALMIC SURGERY

TECHNICAL FIELD

The present invention relates to a training device for ophthalmic surgery as used for training of inner limiting membrane peeling (ILM peeling) in vitreous surgery.

BACKGROUND ART

There is an ocular disease called macular hole, in which a small circular hole is created at the center of retina, resulting in a decrease in visual acuity. A macular hole treatment protocol involves vitreous surgery in which the vitreous body near the retina is resected, the circular hole-surrounding inner limiting membrane is peeled, and gas is then injected intraocularly. At this time, the ILM peeling is performed because the peeling facilitates proliferation of glial cells near the circular hole to exert an effect of promoting closure of the circular hole.

Unfortunately, the ILM peeling is hard to practice even if an animal eye is used. Thus, it is essential to acquire this technique by accumulating experience in clinical settings. However, there is a concern about conducting a fine operation, such as ILM peeling, in clinical settings at the first time. On top of that, it is difficult to obtain many practice opportunities until the technical learning has been completed.

Here, WO 2015/151939A discloses an ILM peeling model fit for technical training of ILM peeling, etc. In WO 2015/151939A, FIG. 6 is a cross-sectional view of this ILM peeling model including an artificial inner limiting membrane having a polymer material as a main component. This ILM peeling model 110 is prepared by layering an artificial inner limiting membrane 120 and an artificial retina 130 on a support base material 140. The artificial inner limiting membrane 120 is produced by including a polymer material as a main component.

In WO 2015/151939A, FIG. 7 is an actual example of a training device for ILM peeling while the ILM peeling model is used. This training device 100 for ILM peeling includes a model set main body 132 having an inlet 131 through which a surgical instrument 133 can be inserted, and is structured such that an ILM peeling model 110 can be set on a lower side. This enables training of peeling the artificial inner limiting membrane 120, which is provided on a surface of the ILM peeling model 110, by using the surgical instrument 133 such as forceps while visually recognizing from the top of the model set main body 132.

Use of such a training device 100 for ILM peeling makes it possible to practice ILM peeling. However, preparation of the ILM peeling model 110 is complicated. Also, the ILM peeling model 110 is, for instance, flat. Thus, there are many differences from actual ILM peeling.

Meanwhile, a research article (Akira Hirata, Ryo Iwakiri, Satoshi Okinami: A simulated eye for vitreous surgery using Japanese quail eggs. Graefe's Archive for Clinical and Experimental Ophthalmology, Volume 251, Issue 6, pp 1621-1624, 2013) discloses a method for practicing ILM peeling while an inner eggshell membrane of a Japanese quail egg is used like an inner limiting membrane and set for a simulated eye. Here, the simulated eye is produced by removing an upper portion of a Japanese quail eggshell with scissors exclusively used for Japanese quail eggs; leaving some contents behind; tightly sealing the egg with a silicone-made simulated sclera; and then filling it with ocular perfusion fluid. Japanese quail eggs share features with simulated eyes because their size is close to those of eyeballs and how one feels when peeling an inner eggshell membrane off a Japanese quail egg resembles ILM peeling. Besides, Japanese quail eggs are inexpensive and commercially available, and are thus easy to prepare. This is an advantage. Specifically, use of a Japanese quail eggshell makes it possible to practice, in a laboratory, ILM peeling in a manner similar to actual practice.

However, for a simulated eye prepared using a Japanese quail egg, the whole Japanese quail egg is simulated as an eyeball. Consequently, it is necessary to conduct operations such as removal of egg yolk and egg white by using, for instance, a vitreous cutter so as to reach an inner eggshell membrane. In addition, perfusion needs the eggshell to be completely sealed. Since individual differences can cause variation in eggshell size, usable eggshells have to be sorted. Besides, when implemented, each egg should be fixed to a base in a state allowing for simulated surgery. There is thus a concern about cracking when fixed to the base. This is also troublesome because careful preparation is required.

SUMMARY OF INVENTION

Technical Problem

In light of such actual situations, the purpose of the present invention is to provide a training device for ophthalmic surgery so as to make it possible to readily practice ILM peeling by using an simulated eye including a Japanese quail eggshell.

Solution to Problem

The present invention provides a training device for ophthalmic surgery, including a base with a hollow portion and a soft simulated sclera member shaped like a part of sphere, in which the hollow portion is tapered from an upper side to a lower side and houses, upon use, a simulated eye including an eggshell; the simulated sclera member is provided on an upper side of the base; and a surgical instrument can contact, through the simulated sclera member, an inner surface of the simulated eye.

Here, the simulated sclera member may have a transparent top section or may have a hole at its top section. In addition, the periphery of the hole may be reinforced using, for instance, silicone or resin. Additionally, the simulated sclera member may have an outer cover provided with a through-hole at its top end and placed on the simulated sclera member.

Also, the present invention provides a training device for ophthalmic surgery, including an annular base with a hollow portion; a soft simulated sclera member shaped like a part of sphere; and a fastener means for fixing the simulated sclera member to the base.

Advantageous Effects of Invention

The training device for ophthalmic surgery according to the invention may include just a few members such as a base, a simulated sclera member, and an outer cover and uses a simulated eye including, for instance, a Japanese quail eggshell, and can thus exert an effect of readily practicing ILM peeling. In addition, the training device for ophthalmic surgery according to the invention can be used to reproduce a feeling of insertion of a surgical instrument into a sclera and excels in the structure that can keep a self-standing sclera sandwiched in a replaceable manner. Further, if a sclera is damaged by a surgical instrument during use of the training device for ophthalmic surgery according to the invention, the damaged sclera can be replaced.

BRIEF DESCRIPTION OF DRAWINGS

FIG. 8A shows a training device for ophthalmic surgery, which device includes a clamper(s) as a fastener means, according to another embodiment.

FIG. 8B shows a training device for ophthalmic surgery, which device includes a screw(s) as a fastener means, according to another embodiment.

FIG. 8C shows a training device for ophthalmic surgery, which device includes a fixing ring as a fastener means, according to another embodiment.

FIG. 8D shows a training device for ophthalmic surgery, which device includes a rubber band as a fastener means, according to another embodiment.

DESCRIPTION OF EMBODIMENTS

Figure 1:
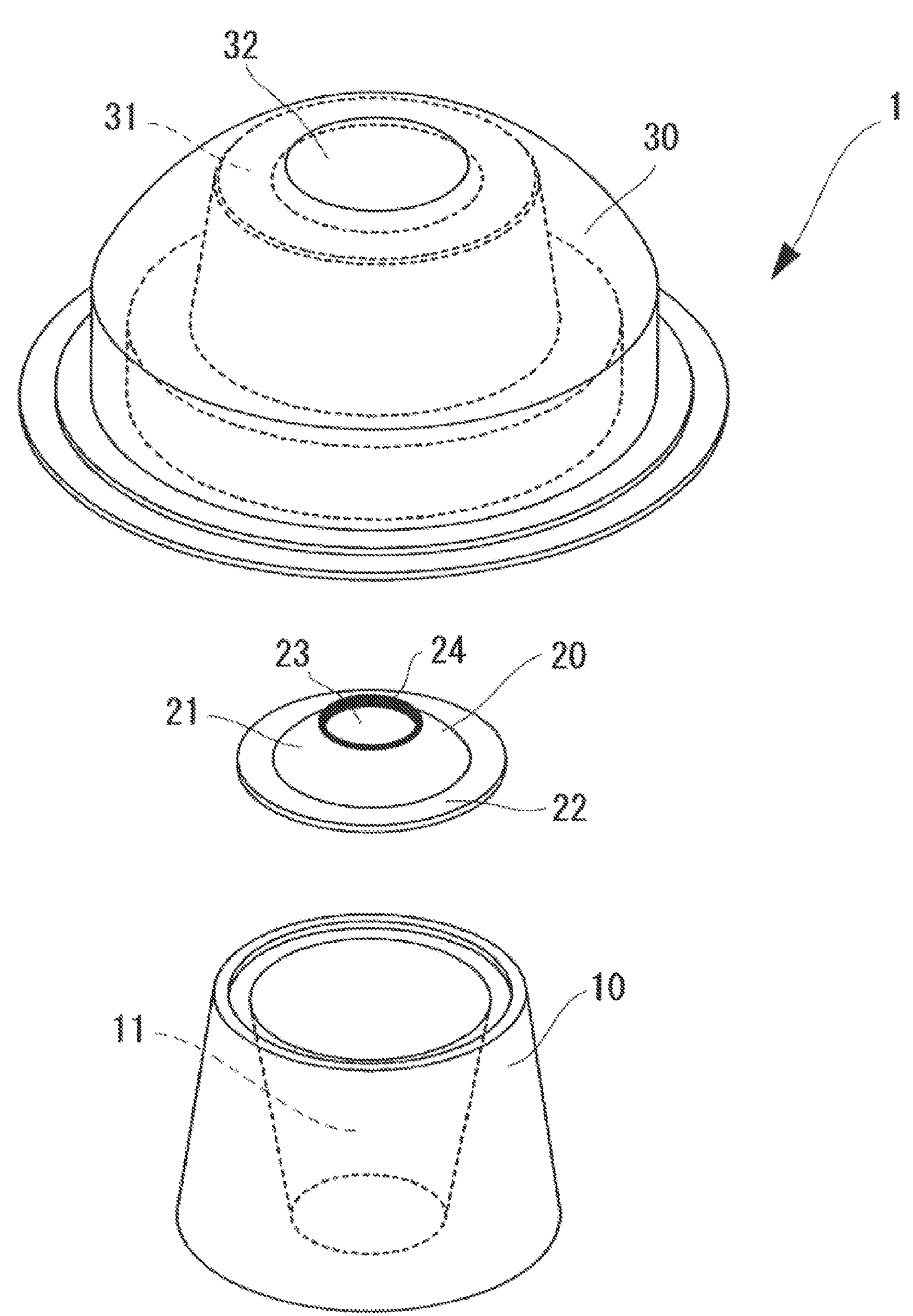
FIG. 1 is an exploded perspective view of a training device for ophthalmic surgery.
Figure 2:
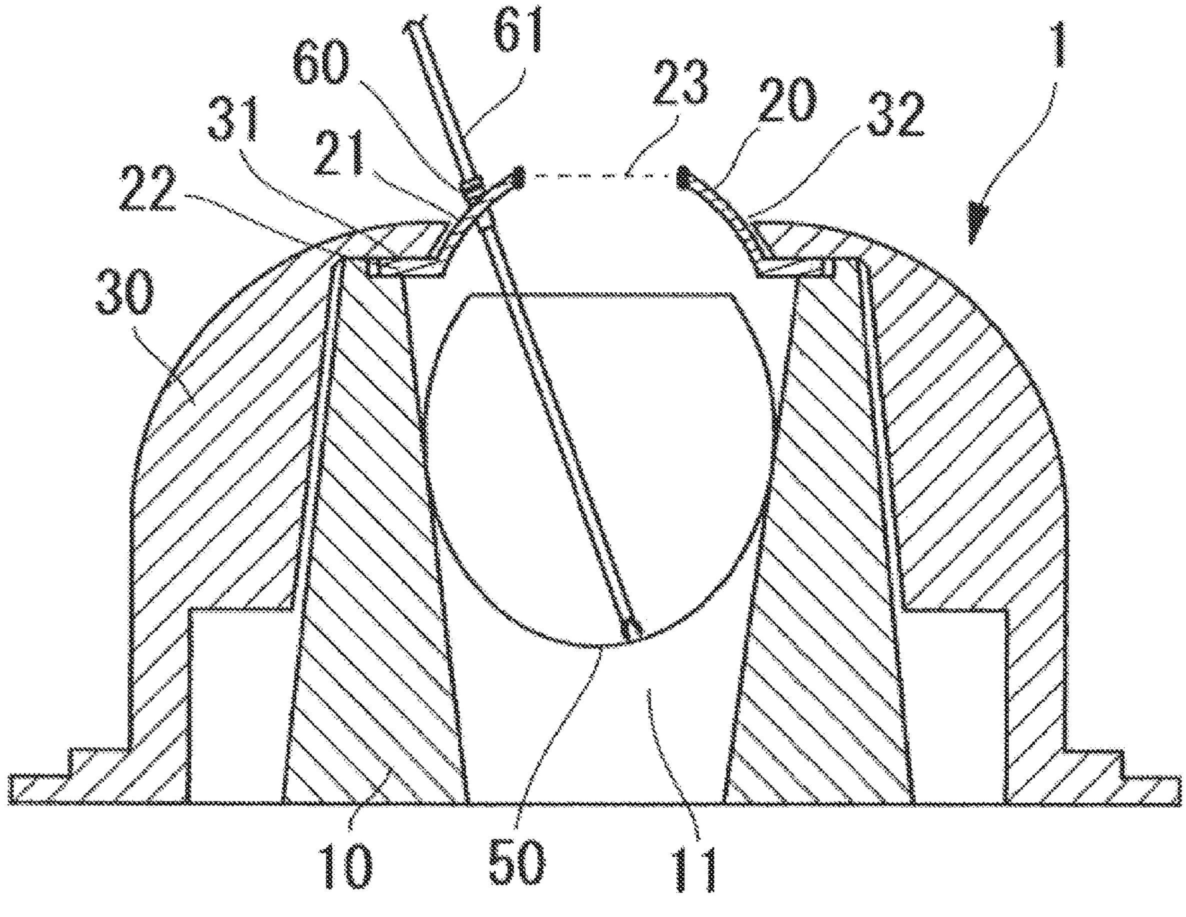
FIG. 2 is a cross-sectional view illustrating a state in which the training device for ophthalmic surgery is used.

Hereinafter, embodiments of the invention will be described with reference to the drawings. FIG. 1 is an exploded perspective view of a training device for ophthalmic surgery. FIG. 2 is a cross-sectional view illustrating a state in which the training device for ophthalmic surgery is used.

A training device 1 for ophthalmic surgery includes three members: a base 10 for housing a simulated eye 50 in a hollow portion 11; a simulated sclera member 20 having a simulated sclera part 21; and an outer cover 30 for holding down the simulated sclera member 20.

It is possible to use a processed Japanese quail eggshell as the simulated eye 50.

Specifically, an upper portion of a Japanese quail eggshell may be excised with regular scissors. Next, the whole content may be removed. Then, an inner eggshell membrane may be stained. After that, the eggshell may be filled with ocular perfusion fluid to produce the simulated eye 50. However, this eggshell is not limited to a Japanese quail eggshell. If vitreous surgery is reproducible using an eggshell like a Japanese quail eggshell, this eggshell can also be used absolutely.

The appearance of the base 10 is shaped like a cylinder or truncated cone having the hollow portion 11. The hollow portion 11 is tapered from an upper side to a lower side. Specifically, the shape is like an inverted cone or inverted, truncated cone having a top opening. The hollow portion 11 houses, upon use, the simulated eye 50. Since the hollow portion 11 is tapered from an upper side to a lower side, the simulated eye 50 can be stopped partway through the hollow portion 11 when inserted from an upper side. At this time, the size of an eggshell corresponding to the simulated eye 50, may vary. Accordingly, the eggshell bottom of each simulated eye 50 may be variously positioned. This makes it possible to reproduce the difference in eye axial length between actual eyeballs. In addition, the simulated eye 50 may be inserted into the hollow portion 11 from an upper side. This makes the setting simple, and there is little concern about cracking.

Figure 3A:
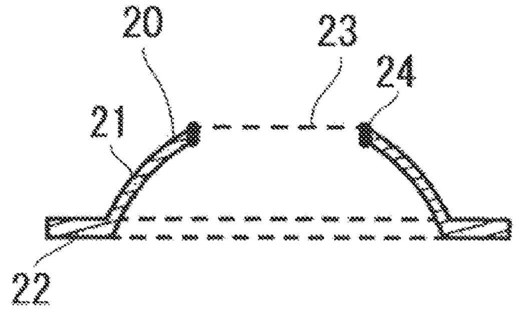
FIG. 3A shows an Example of a simulated sclera member having a hole at its top section.
Figure 3A:
Figure 3B:
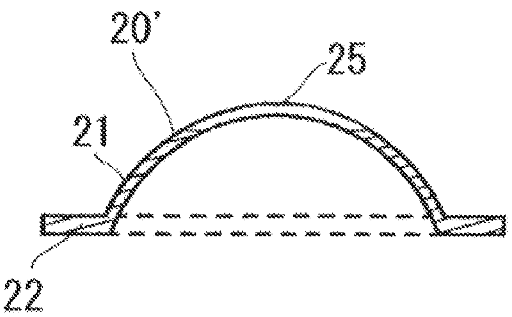
FIG. 3B shows an Example of a simulated sclera member without a hole at its top section.

The simulated sclera member 20 is mounted on the base 10 and used as a simulated sclera. FIG. 3A shows an Example of the simulated sclera member 20 having a hole 23 at its top section. FIG. 3B shows an Example of a simulated sclera member 20' without a hole at its top section.

The simulated sclera member 20 or 20' is made of soft material such as silicone and include: a simulated sclera part 21 shaped like a part of sphere; and a hollow disk-shaped edge part 22 that extends outward at the bottom end of the simulated sclera part 21. During surgery training, the edge part 22 is placed to contact an upper side of the base 10 upon use. That is, the simulated sclera part 21 is positioned directly over the simulated eye 50. Note that the upper side of the base 10 may be provided with a groove fit for the edge part 22. This defines the set position of the simulated sclera member 20 or 20'. Further, their dislocation can be suppressed.

The simulated sclera part 21 is shaped like a part of sphere, the curvature of which may be adjusted to the average eyeball size of human eyes. In addition, the simulated sclera part 21 is made of soft material such as silicone, so that a cannula 60 may be attached. Thus, during surgery training, the cannula 60 can be attached to the simulated sclera part 21. Then, a surgical instrument 61 such as forceps may be inserted through the cannula 60 to reproduce a state of insertion into an eyeball. Specifically, this can mimic a state in which one has the surgical instrument 61 penetrate through the simulated sclera member 20 or 20' to be able to contact an inside surface of the simulated eye 50.

Here, a top section of the simulated sclera member 20 or 20' corresponds to the position of cornea of an eyeball. That is, during surgery training, the inside of the simulated eye 50 can be visually checked through the top section of the simulated sclera member 20 or 20'. Meanwhile, Examples include the simulated sclera member 20 or 20' with or without a hole 23 at its top section. In the case of the simulated sclera member 20' without a hole, the top section should be transparent such that the inside can be visually recognized. Specifically, the simulated sclera member 20' without a hole at its top section is provided with a simulated cornea part 25 with a transparent top section.

By contrast, in the case of the simulated sclera member 20 having a hole 23, as a simulated cornea part, at its top section, the periphery of the hole 23 is provided with a reinforcing part 24 that is reinforced using, for instance, a resin or adhesive or silicone having a thickness larger than those of other positions of the simulated sclera part 21. Without such a reinforcing part 24, it is highly likely that when the cannula 60 is attached to the simulated sclera part 21 or the surgical instrument 61 is moved, the simulated sclera part 21 is deformed. Specifically, when the periphery of the hole 23 is provided with the reinforcing part 24, it is possible to prevent the simulated sclera part 21 from being indented at the time of attachment of the cannula 60 or to prevent the simulated sclera part 21 from being distorted or dislocated in response to the movement of the surgical instrument 61 such as inserted forceps. This can make simulated surgery highly reproducible.

Further, the outer cover 30 covers and holds down the simulated sclera member 20 or 20'. This can suppress dislocation of the simulated sclera member 20 or 20'. How to hold down the simulated sclera member 20 or 20' involves a structure where a portion of the outer cover 30 is placed on the upper surface of the edge part 22 of the simulated sclera member 20 or 20'. The portion placed on the upper surface of the edge part 22 is called an edge stopper portion 31. In this way, the weight of the outer cover 30 can restrict the dislocation of the simulated sclera member 20 or 20'. In addition, the top end of the outer cover 30 has a through-hole 32. The simulated sclera part 21 of the simulated sclera member 20 or 20' fits this through-hole 32 and is set to protrude outwardly.

Figure 4A:
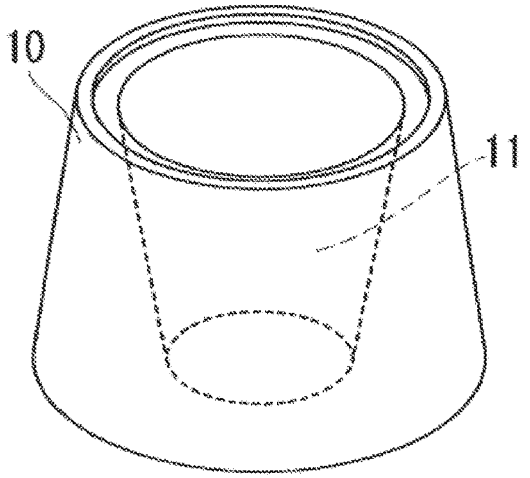
FIG. 4A shows an Example of a base having an opening on its upper face and having a hollow portion shaped like an inverted, truncated cone.
Figure 4B:
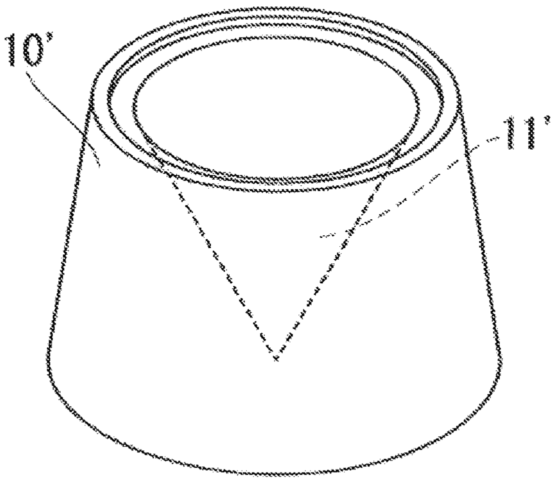
FIG. 4B shows an Example of a base having an opening on its upper face and having a hollow portion shaped like an inverted cone.

FIGS. 4A and 4B illustrate Examples of bases 10 and 10', respectively. The base 10 or 10' needs a hollow portion 11 or 11' in which the simulated eye 50 made of a Japanese quail eggshell can be housed. FIG. 4A shows an Example of the base 10 having a top opening and having a hollow portion 11 shaped like an inverted, truncated cone. FIG. 4B shows an Example of the base 10' having a top opening and having a hollow portion 11' shaped like an inverted cone. The shape of the hollow portion is not limited to these Examples. There is no problem as long as the hollow portion is tapered from an upper side to a lower side and can house a Japanese quail eggshell. Here, the slope and size of the inverted, truncated cone or the inverted cone may be determined such that a Japanese quail eggshell can be housed and the distance from the cannula 60 to the eggshell bottom substantially agrees with the variation in eye axial length among human eyes.

Figure 5:
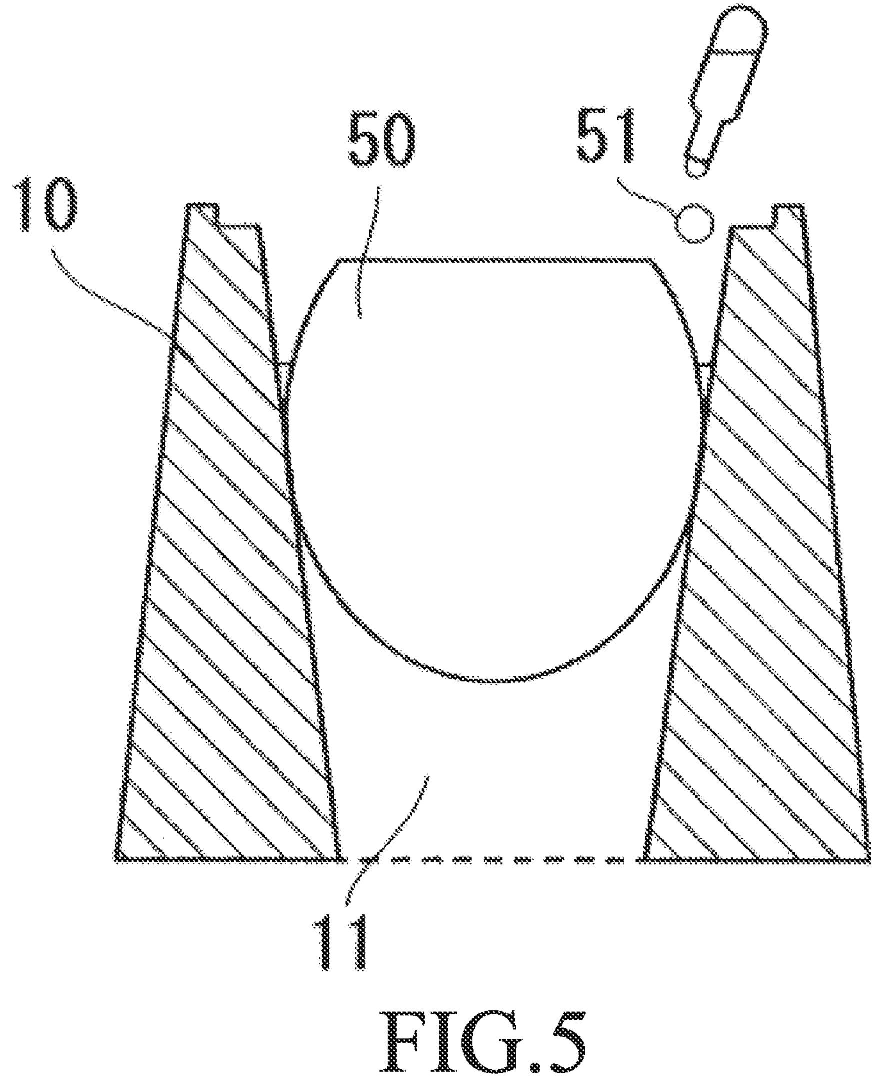
FIG. 5 is a cross-sectional view when a base houses a simulated eye.
Figure 6:
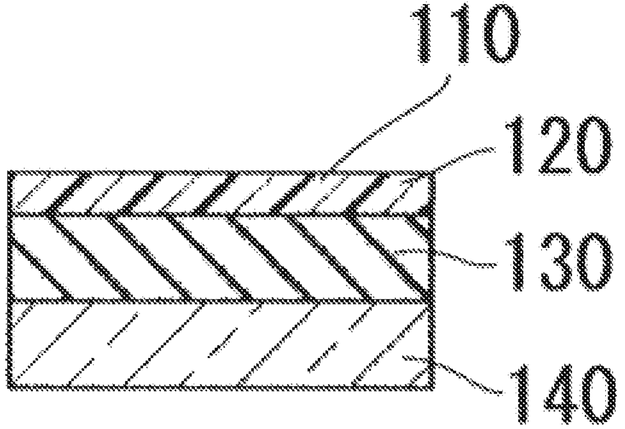
FIG. 6 is a cross-sectional view of an ILM peeling model including an artificial inner limiting membrane having a polymer material as a main component.
Figure 7:
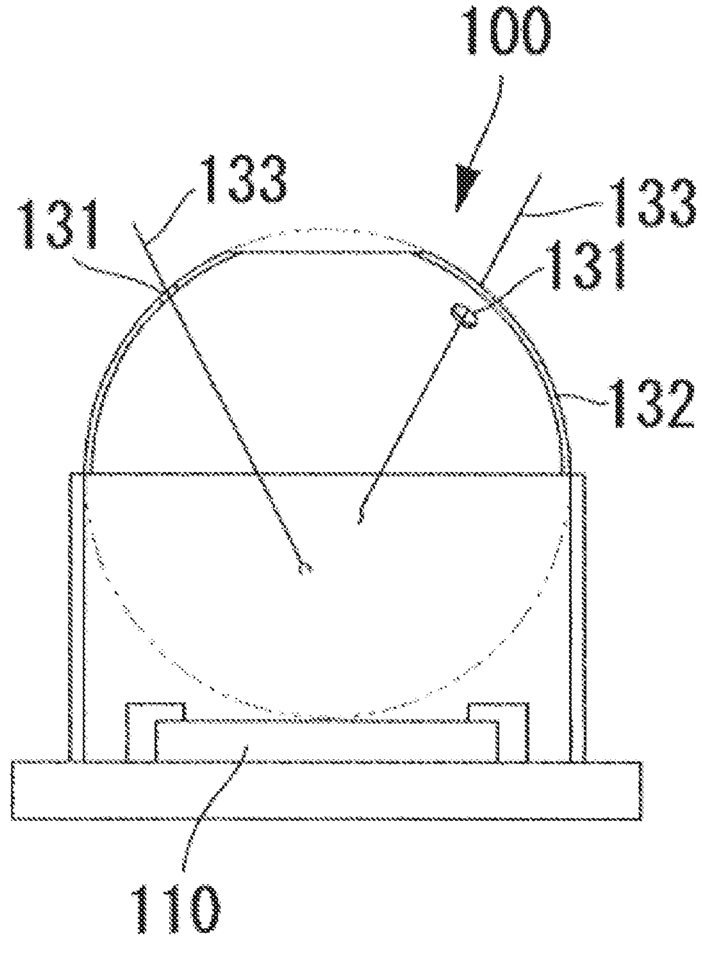
FIG. 7 is an actual example of a training device for ILM peeling while an ILM peeling model is used.

FIG. 5 is a cross-sectional view when the base houses a simulated eye. The cross-sectional view, in which the base 10 having an inverted, truncated cone-shaped hollow portion 11 is used, is herein used for description. Of course, it is possible to use the base 10' having an inverted cone-shaped hollow portion 11'. When the simulated eye 50 is housed in such an inverted, truncated cone-shaped or inverted cone-shaped hollow portion 11, it is considered difficult to stabilize the simulated eye 50 because of, for instance, rotation. Thus, to stabilize the simulated eye 50 when housed, a small amount of water 51 may be filled into a gap between the hollow portion 11 and the simulated eye 50. This facilitates the simulated eye 50 to be housed without any gap between the hollow portion 11 and the simulated eye 50, thereby capable of stabilizing the simulated eye 50 by means of the surface tension of the water 51 retained in the gap.

A simulated eye including a Japanese quail eggshell was set on the above training device for ophthalmic surgery, and physicians were instructed to use the device. Then, they found a feeling very close to that during clinical use, such as how to operate an instrument and/or how the inner limiting membrane behaved. In addition, when an eggshell in a stained condition was provided, the eggshell was successfully set on the training device for ophthalmic surgery within about 30 sec. Further, it was found that the observation was fully possible by using either a surgical microscope or binocular stereomicroscope. Hence, use of the training device for ophthalmic surgery according to the invention makes it possible to use a readily available Japanese quail eggshell as a simulated eye. Collectively, the results obtained have revealed that a training environment for ILM peeling can be realized in a simple and reproducible manner.

FIGS. 8A to 8D show training devices (1' to 1"") for ophthalmic surgery according to other embodiments. Each training device (1' to 1"") for ophthalmic surgery illustrated in FIGS. 8A to 8D includes: an annular base 10 with a hollow portion 11; a soft simulated sclera member 20 shaped like a part of sphere; and a fastener means (101 to 104) for fixing the simulated sclera member 20 to the base 10. The fastener means illustrated in FIG. 8A is a clamper(s) 101. The simulated sclera member 20 is fixed to the base 10 while a part of the damper 101 is bent. The fastener means illustrated in FIG. 8B is a screw(s) 102. The simulated sclera member 20 is fixed to the base 10 while the screw 102 is screwed in the arrowhead direction. The fastener means illustrated in FIG. 8B may be a pin(s). The simulated sclera member 20 is fixed to the base 10 while the pin is drilled in the arrowhead direction. The fastener means illustrated in FIG. 8C is a fixing ring 103. The fixing ring 103 can be split into 2 parts. The simulated sclera member 20 is fixed to the base 10 while the respective parts of the fixing ring 103 are joined such that the simulated sclera member 20 and the base 10 are interposed therebetween. The fastener means illustrated in FIG. 8D is a rubber band 104. The simulated sclera member 20 is fixed to the base 10 by using rubber band 104 contraction force in the base 10 direction. Each training device for ophthalmic surgery (1' to 1"") is applicable to training of ophthalmic surgery using an ophthalmic tool (e.g., an intraocular lens) other than simulated eyes and training of ophthalmic surgery in the anterior ocular segment (e.g. scleral wound dehiscence, trocar deployment). Each training device for ophthalmic surgery (1' to 1"") is or is not necessarily provided beforehand with a simulated eye. The device may be provided with an alternative (e.g., a simulated eye having a crystalline lens) other than the simulated eye including an eggshell.

REFERENCE SIGNS LIST

1, 1', 1", 1'", 1"" Training device for ophthalmic surgery
10, 10' Base
11, 11' Hollow portion
20, 20' Simulated sclera member
21 Simulated sclera part
22 Edge part
23 Hole
24 Reinforcing part
25 Simulated cornea part
30 Outer cover
31 Edge stopper portion
32 Through-hole
50 Simulated eye (including a Japanese quail eggshell)
51 Water
60 Cannula
61 Surgical instrument
101, 102, 103, 104 Fastener means

The invention claimed is:

1. A training device for ophthalmic surgery, comprising:

a base with an inverted, truncated cone-shaped hollow portion, the inverted, truncated cone-shaped hollow portion being tapered from an upper side to a lower side and configured to receive a simulated sub-portion of an eye including an outer shell composed of an eggshell on an inner surface of the inverted, truncated cone-shaped hollow portion of the base;

a soft simulated sclera member shaped like a part of a sphere, and a fastener means for fixing the simulated sclera member on an upper side of the base, wherein:

the soft simulated sclera member can be replaced, and a surgical instrument can contact, through the simulated sclera member, a surface of the simulated sub-portion of the eye.

2. The training device according to claim 1, wherein the simulated sclera member has a transparent top section.

3. The training device according to claim 1, wherein the simulated sclera member has a hole at a top section thereof and the hole has a reinforced periphery.

4. The training device according to claim 1, further comprising an outer cover provided with a through-hole at a top end thereof and placed on the simulated sclera member.

5. A training device for ophthalmic surgery, comprising:

an annular base with a hollow portion, the hollow portion having an opening at an upper end of the hollow portion;

a soft simulated sclera member shaped like a part of a sphere; and a fastener means for fixing the simulated sclera member to the base, wherein: the soft simulated sclera member can be replaced by removing the fastener means, the simulated sclera member comprises a simulation sclera part and a hollow disk-shaped edge part that extends outward at a bottom end of the simulated sclera part; and the hollow disk-shaped edge part of the simulated sclera member is provided on an upper side of the base.

* * * * *